(12) United States Patent
Zheng et al.

(10) Patent No.: US 11,371,921 B1
(45) Date of Patent: Jun. 28, 2022

(54) CLAMP AND SHEAR TEST DEVICE

(71) Applicant: Institute of Geology and Geophysics, Chinese Academy of Sciences, Beijing (CN)

(72) Inventors: Bowen Zheng, Beijing (CN); Shengwen Qi, Beijing (CN); Songfeng Guo, Beijing (CN); Xiaolin Huang, Beijing (CN); Ning Liang, Beijing (CN); Guangming Luo, Beijing (CN); Yu Zou, Beijing (CN); Shuaihua Song, Beijing (CN); Zhendong Cui, Beijing (CN); Lei Xue, Beijing (CN); Guoliang Li, Beijing (CN); Tianming Huang, Beijing (CN); Yiman Li, Beijing (CN); Yanhui Dong, Beijing (CN); Liheng Wang, Beijing (CN); Guiyang Ren, Beijing (CN); Qingze Hao, Beijing (CN); Libo Jiang, Beijing (CN); Xin Wang, Beijing (CN); Wenjiao Xiao, Beijing (CN)

(73) Assignee: Institute of Geology and Geophysics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 17/533,876

(22) Filed: Nov. 23, 2021

(30) Foreign Application Priority Data

Jun. 25, 2021 (CN) .......................... 202110707117.3

(51) Int. Cl.
*G01N 3/02* (2006.01)
*G01N 3/24* (2006.01)
*G01N 33/24* (2006.01)

(52) U.S. Cl.
CPC ................. *G01N 3/02* (2013.01); *G01N 3/24* (2013.01); *G01N 33/24* (2013.01); *G01N 2203/0025* (2013.01)

(58) Field of Classification Search
CPC ...... G01N 3/02; G01N 3/24; G01N 33/24; G01N 2203/0025; G01N 3/10; G01N 3/00; G01N 19/04; E02D 1/02; G01B 11/25
See application file for complete search history.

(56) References Cited

U.S. PATENT DOCUMENTS

| 7,051,600 B1 * | 5/2006 | Cavallaro | G01N 3/08 73/862.041 |
|---|---|---|---|
| 10,876,944 B1 * | 12/2020 | Zheng | G01N 3/02 |
| 2020/0124510 A1 * | 4/2020 | Ma | G01N 3/32 |

FOREIGN PATENT DOCUMENTS

| CN | 207096004 U | 3/2018 |
|---|---|---|
| CN | 110411822 A | 11/2019 |
| CN | 113252472 B | 9/2021 |

OTHER PUBLICATIONS

First office Action dated Aug. 20, 2021 for CN 202110717117.3.
Notification to Grant Patent Right for Invention dated Sep. 1, 2021 issued for CN202110707117.3.

* cited by examiner

*Primary Examiner* — Brandi N Hopkins
(74) *Attorney, Agent, or Firm* — Hunton Andrews Kurth LLP

(57) ABSTRACT

A clamp and a shear test device are provided, and relate to the technical field of rock mass mechanics tests. The clamp comprises a box body, wherein an opening is formed in one side of the box body, two clamping structures are oppositely arranged in the box body, a sample is arranged between the two clamping structures, each clamping structure comprises an adjusting mechanism, and a distance between the two clamping structures is adjusted through adjusting mecha- (Continued)

nisms of the two clamping structures. According to the clamp, real-time dynamic adjustment is conveniently and rapidly achieved, the stability of sample clamping is ensured, and therefore the requirement that the shear load can be truly and effectively transmitted to the sample through the box body is met.

12 Claims, 10 Drawing Sheets

CLAMP AND SHEAR TEST DEVICE

CROSS REFERENCE TO RELATED APPLICATION

This patent application claims the benefit and priority of Chinese Patent Application No. 202110707117.3 filed on Jun. 25, 2021, the disclosure of which is incorporated by reference herein in its entirety as part of the present application.

TECHNICAL FIELD

The present disclosure relates to the technical field of rock mass mechanics tests, and particularly relates to a clamp and a shear test device.

BACKGROUND ART

Sedimentary rocks and parametamorphic rocks are widely distributed in nature, and the deformation and damage of the sedimentary rocks and the parametamorphic rocks are extremely common in rock mass engineering such as tunnels and slopes. The rock mass of the sedimentary rocks and the parametamorphic rocks forms discontinuities with different properties under the action of diagenetic construction and later-period transformation, and the existence of the discontinuities causes strong anisotropic characteristics of the rock mass, and the strong anisotropic characteristics are mainly represented as different physical mechanical behaviors of the rock mass along with the different occurrence states of the layered discontinuities. Rock mass mechanical behaviors, especially shear characteristics, of the sedimentary rocks and the parametamorphic rocks are quite complex, and influence on engineering stability of rock mass is large; and therefore, indoor shear tests need to be widely developed urgently to describe anisotropic characteristics of rock mass shear behaviors of the sedimentary rocks and the parametamorphic rocks quantitatively.

The Chinese patent with the publication number of CN207096004U provides a shear box for testing the shear anisotropy of a rock mass structural plane, but the patent does not disclose how to eliminate a gap between a rock mass structural plane sample and the shear box. The Chinese patent with the publication number of CN110411822A provides a shear box for testing the cyclic shear characteristic of a rock mass discontinuity, introduces and explains a technology for eliminating a gap of a rock mass discontinuity sample in a clamping process through a specific device in the shear box before a test, but the patent does not disclose dynamic adjustment of the gap during the test process. Therefore, real-time dynamic adjustment of a sample clamping gap in the whole process of the rock mass structural plane shear test of sedimentary rocks or parametamorphic rocks cannot be realized.

SUMMARY

The present disclosure aims to provide a clamp and a shear test device to solve the problems exiting in the prior art, so that distance between two clamping structures can be adjusted in real time, and the stability of sample clamping is ensured.

In order to achieve the purpose, the present disclosure provides the following scheme:

The present disclosure provides a clamp. The clamp comprises a box body, wherein an opening is formed in one side of the box body, two clamping structures are oppositely arranged in the box body, a sample is arranged between the two clamping structures, each clamping structure comprises an adjusting mechanism, and a distance between the two clamping structures is adjusted through adjusting mechanisms of the two clamping structures.

In some embodiments, each clamping structure comprises a first clamping block, a second clamping block, a third clamping block and a fourth clamping block, the first clamping block and the second clamping block are oppositely arranged, the third clamping block and the fourth clamping block are oppositely arranged, the first clamping block is in contact with the third clamping block and the fourth clamping block, the second clamping block is in contact with the third clamping block and the fourth clamping block, the third clamping block and the fourth clamping block are located between the first clamping block and the second clamping block, the sample is located between the first clamping blocks of the two clamping structures, the second clamping blocks of the two clamping structures are both connected with the box body, and the adjusting mechanism is used for adjusting a distance between the third clamping block and the fourth clamping block so as to adjust a distance between the first clamping block and the second clamping block.

In some embodiments, at least one elastic component and at least one guide shaft are arranged between the first clamping block and the second clamping block, one end of the elastic component is connected with the first clamping block, other end of the elastic component is connected with the second clamping block, and the guide shaft is in sliding connection with the first clamping block and the second clamping block.

In some embodiments, the adjusting mechanism is a two-way screw rod, the two-way screw rod is passed through and arranged in the third clamping block and the fourth clamping block, a first threaded section of the two-way screw rod is in threaded connection with the third clamping block, a second threaded section of the two-way screw rod is in threaded connection with the fourth clamping block, the first threaded section and the second threaded section are opposite in screw directions, two ends of the two-way screw rod extend into through holes in side walls of the box body, and the two-way screw rod rotates through bolt devices to adjust the distance between the third clamping block and the fourth clamping block.

In some embodiments, the first clamping block and the second clamping block are same in structures, each of the first clamping block and the second clamping block comprises a first inclined plane and a second inclined plane, the third clamping block and the fourth clamping block are same in structures, each of the third clamping block and the fourth clamping block comprises a third inclined plane and a fourth inclined plane, the first inclined plane of the first clamping block is in contact with the third inclined plane of the third clamping block, the second inclined plane of the first clamping block is in contact with the third inclined plane of the fourth clamping block, the first inclined plane of the second clamping block is in contact with the fourth inclined plane of the third clamping block, and the second inclined plane of the second clamping block is in contact with the fourth inclined plane of the fourth clamping block.

In some embodiments, the first inclined plane and the second inclined plane are symmetrical along a center line of the first clamping block or the second clamping block, and the third inclined plane and the fourth inclined plane are symmetrical along a center line of the third clamping block or the fourth clamping block.

In some embodiments, cross sections of the third clamping block and the fourth clamping block are trapezoidal.

In some embodiments, two fixed blocks are oppositely arranged between the two clamping structures, the two fixed blocks are both in sliding connection with the box body, the sample is arranged between the two fixed blocks, and a cavity formed by the two fixed blocks is matched with a shape of the sample.

In some embodiments, protrusions are arranged on two sides of each fixed block and located in sliding grooves in side walls of the box body.

The present disclosure also provides a shear test device comprising two clamps, openings of two clamps are oppositely arranged, and a gap is formed between the two clamps.

Compared with the prior art, the present disclosure has the following technical effects:

According to the clamp, real-time dynamic adjustment can be conveniently and rapidly achieved, the stability of sample clamping is ensured, and therefore the requirement that the shear load can be truly and effectively transmitted to the sample through the box body is met.

BRIEF DESCRIPTION OF THE DRAWINGS

To more clearly illustrate the embodiment of the present disclosure or the technical scheme in the prior art, the following briefly introduces the attached figures to be used in the embodiment. Apparently, the attached figures in the following description show merely some embodiments of the present disclosure, and those skilled in the art may still derive other drawings from these attached figures without creative efforts.

Reference signs: 100, clamp; 200, shear test device; 1, box body; 2, opening; 3, clamping structure; 4, sample; 5, adjusting mechanism; 6, first claming block; 7, second clamping block; 8, third clamping block; 9, fourth clamping block; 10, elastic component; 11, guide shaft; 12, through hole; 13, first inclined plane; 14, second inclined plane; 15, third inclined plane; 16, fourth inclined plane; 17, fixed block; 18, cavity; 19, protrusion; 20, sliding groove; and 21, bolt structure.

DETAILED DESCRIPTION OF THE EMBODIMENTS

The following clearly and completely describes the technical scheme in the embodiments of the present disclosure with reference to the attached figures in the embodiments of the present disclosure. Apparently, the described embodiments are merely a part rather than all of the embodiments of the present disclosure. Based on the embodiment in the present disclosure, all other embodiments obtained by the ordinary skill in the art without creative labor belong to the scope protected by the present disclosure.

The present disclosure aims to provide a clamp and a shear test device to solve the problems exiting in the prior art, so that the distance between two clamping structures can be adjusted in real time, and the stability of sample clamping is ensured.

To make the foregoing objective, features and advantages of the present disclosure clearer and more comprehensible, the present disclosure is further described in detail below with reference to the attached figures and specific embodiments.

Embodiment I

Figure 1:
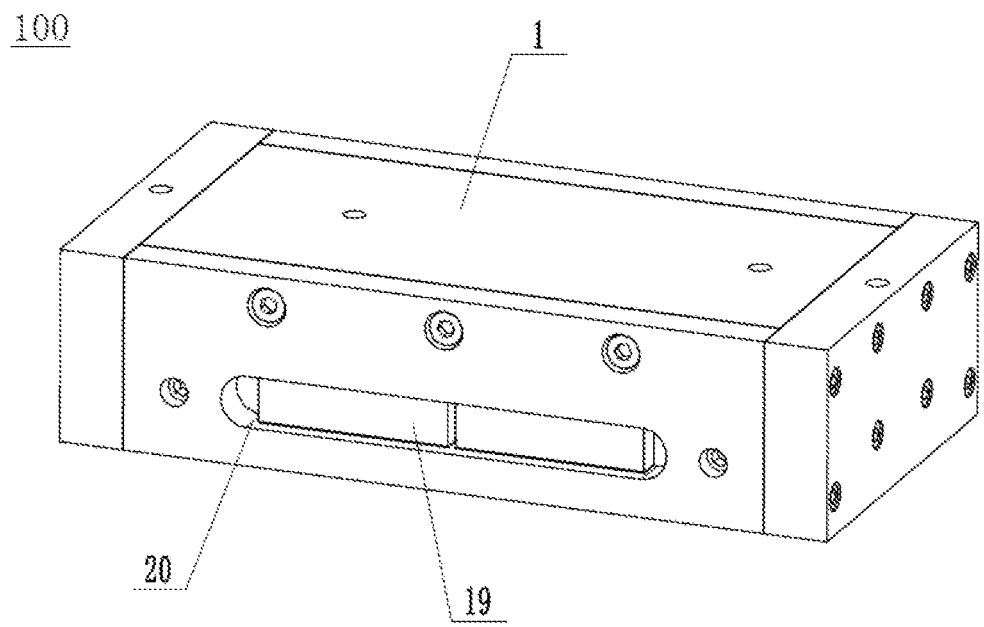
FIG. 1 is a schematic diagram of a clamp in the present disclosure.
Figure 2:
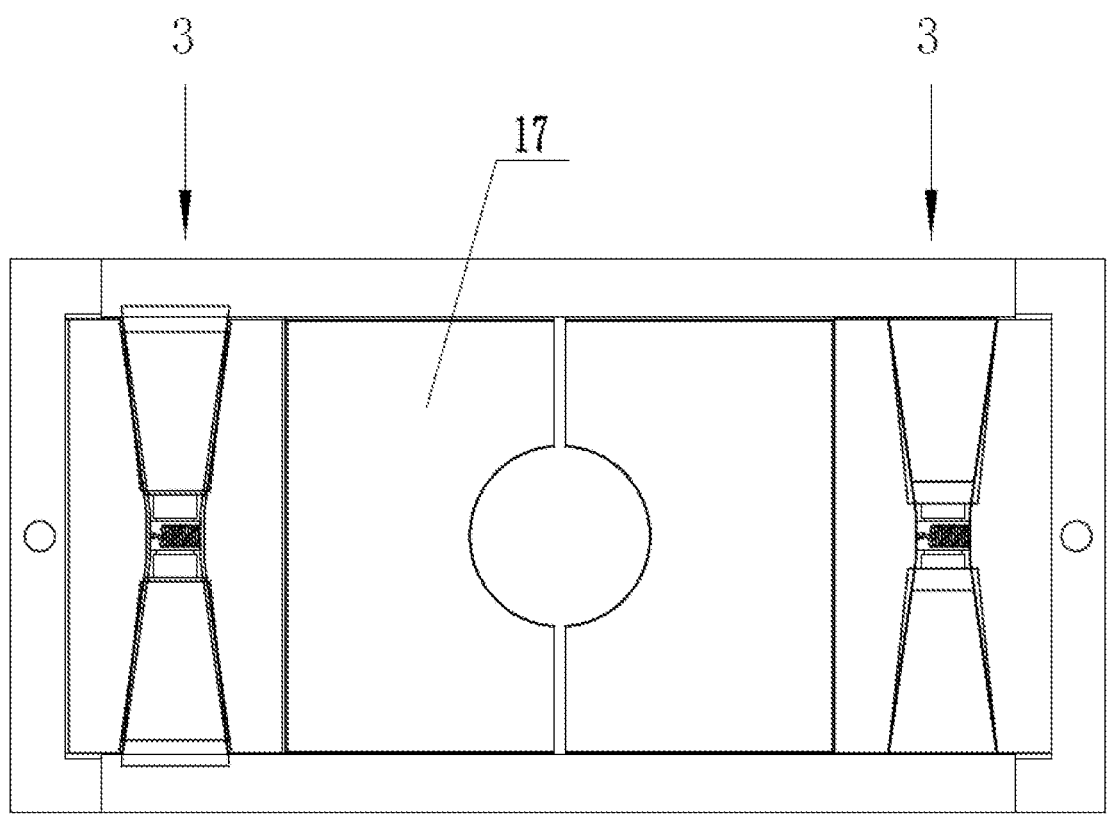
FIG. 2 is a schematic diagram of an internal structural of a clamp in the present disclosure.
Figure 3:
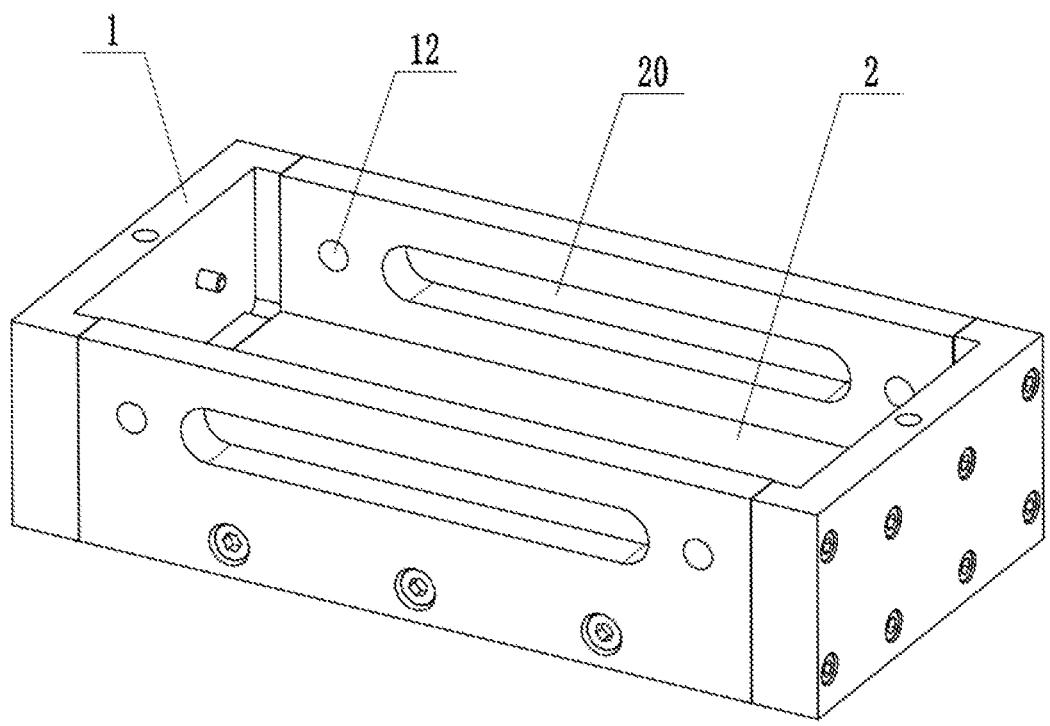
FIG. 3 is a schematic diagram of a box body in the present disclosure.
Figure 4:
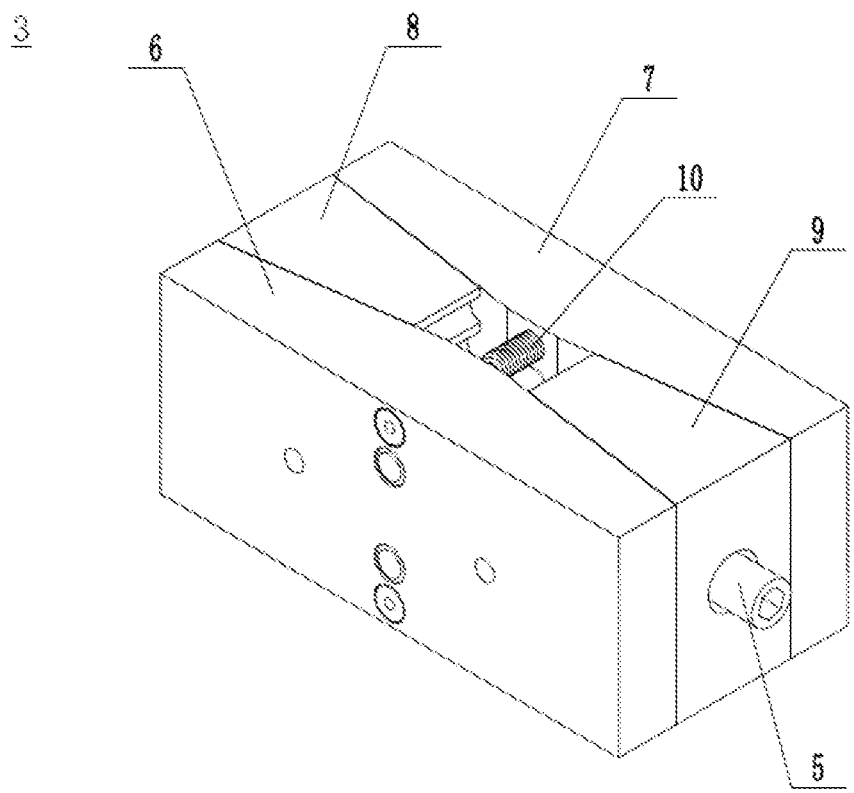
FIG. 4 is a schematic diagram of a clamping structure in the present disclosure.
Figure 5:
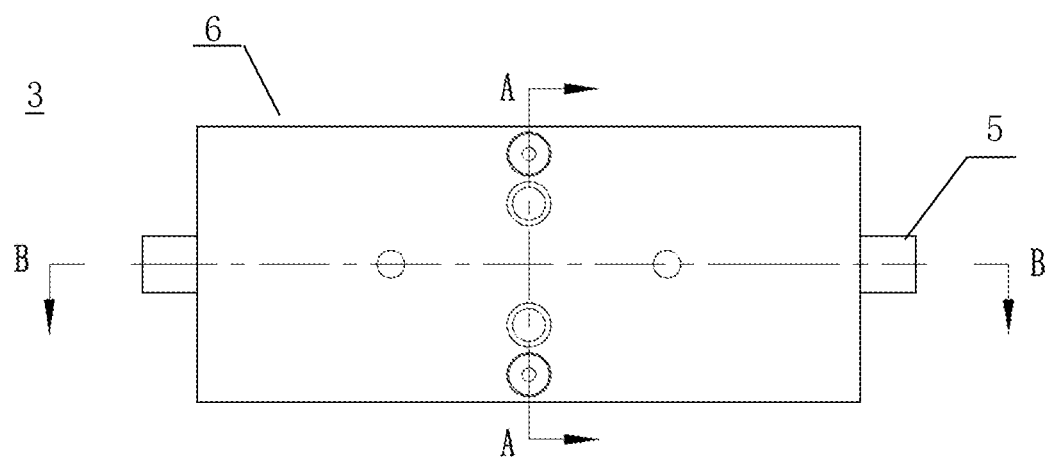
FIG. 5 is a front view of a clamping structure in the present disclosure.
Figure 6:
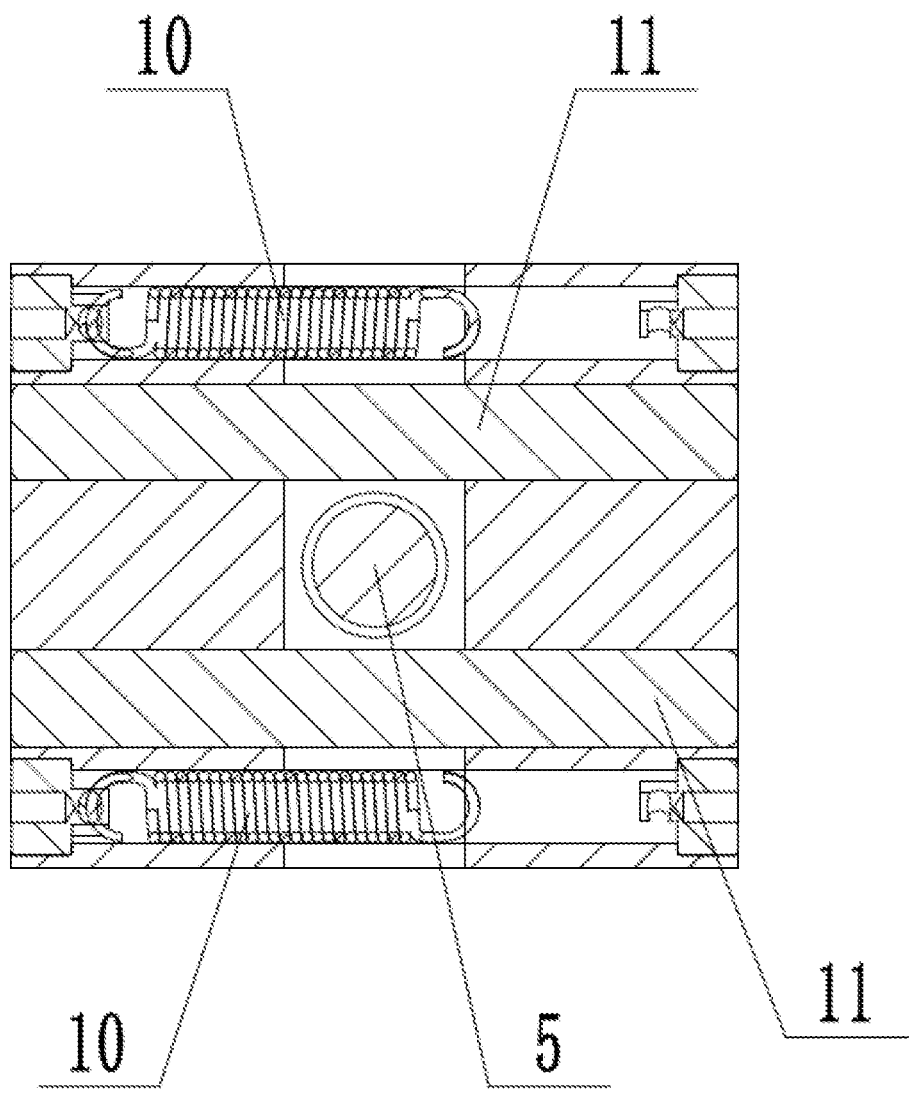
FIG. 6 is a cross-sectional view along the line A-A of FIG. 5.
Figure 7:
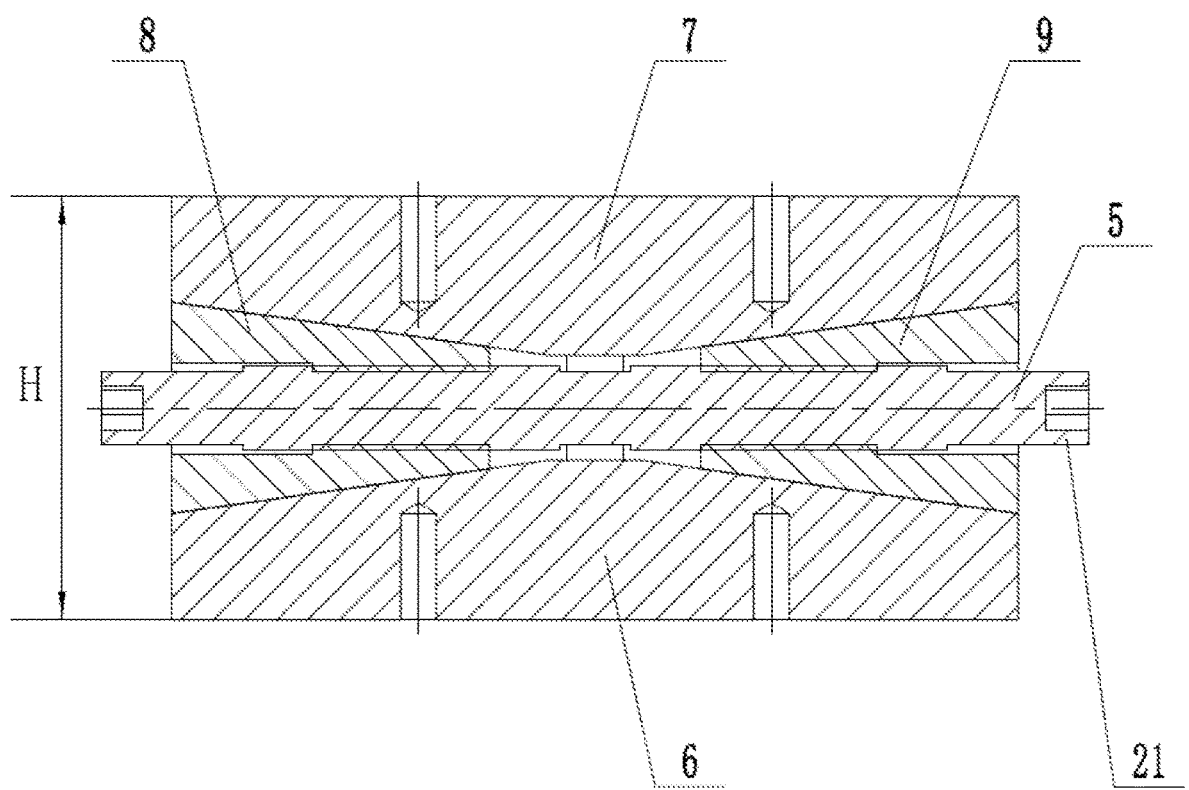
FIG. 7 is a cross-sectional view along the line B-B of FIG. 5.
Figure 8:
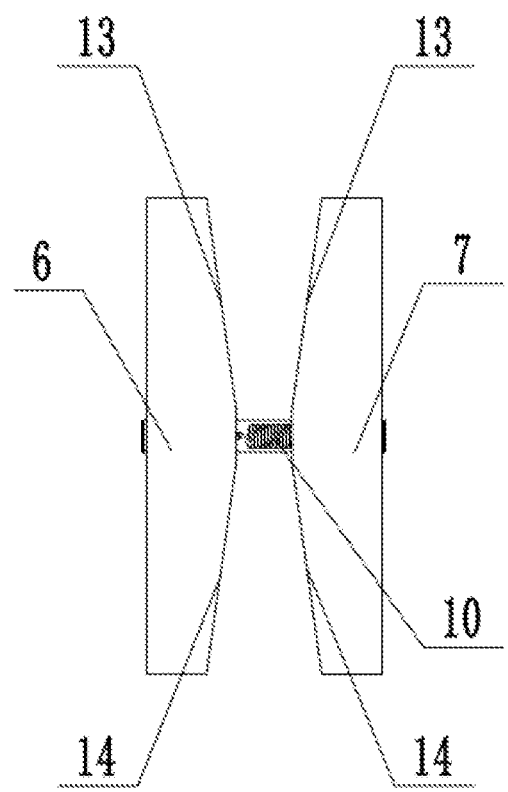
FIG. 8 is a top view of a first clamping block and a second clamping block in the present disclosure.
Figure 9:
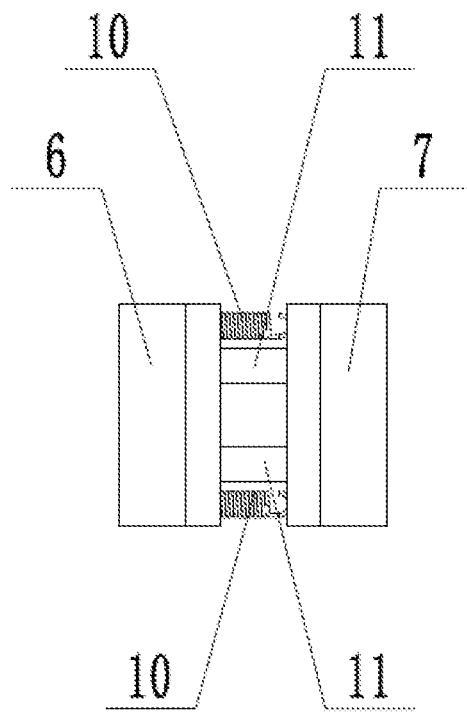
FIG. 9 is a side view of a first clamping block and a second clamping block in the present disclosure.
Figure 10:
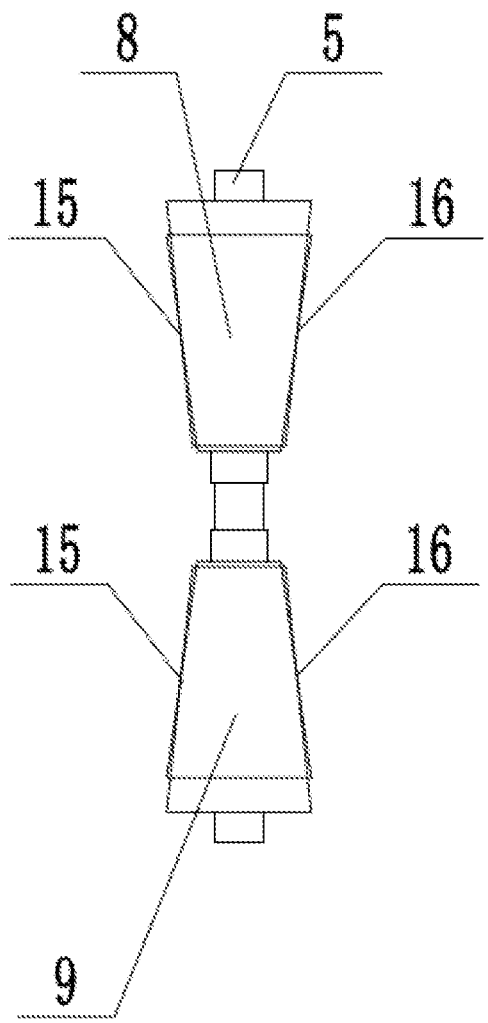
FIG. 10 is a top view of a third clamping block and a fourth clamping block in the present disclosure.
Figure 11:
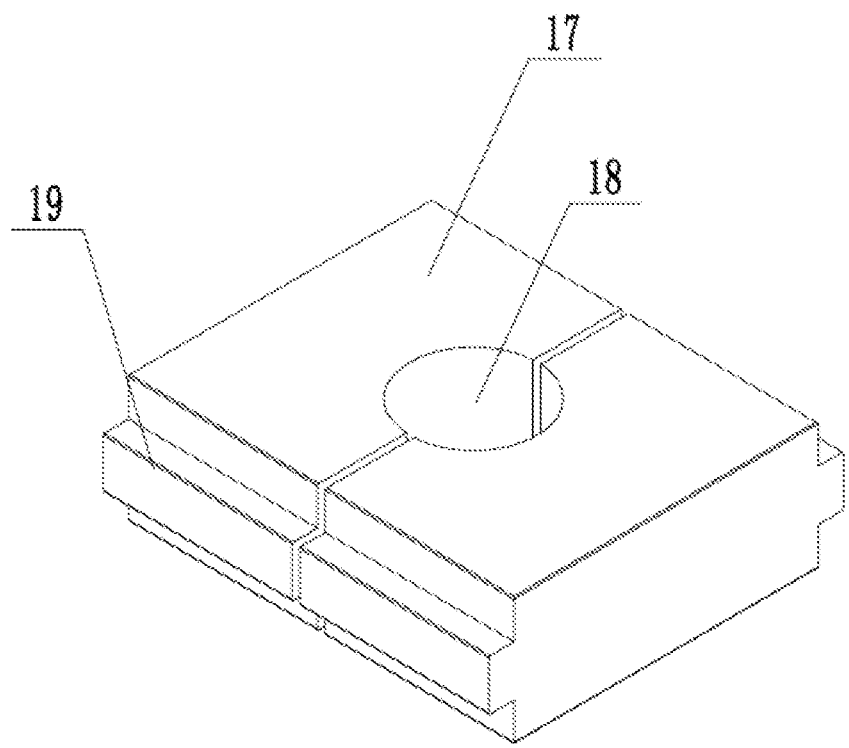
FIG. 11 is a first schematic diagram of a fixed block in the present disclosure.
Figure 12:
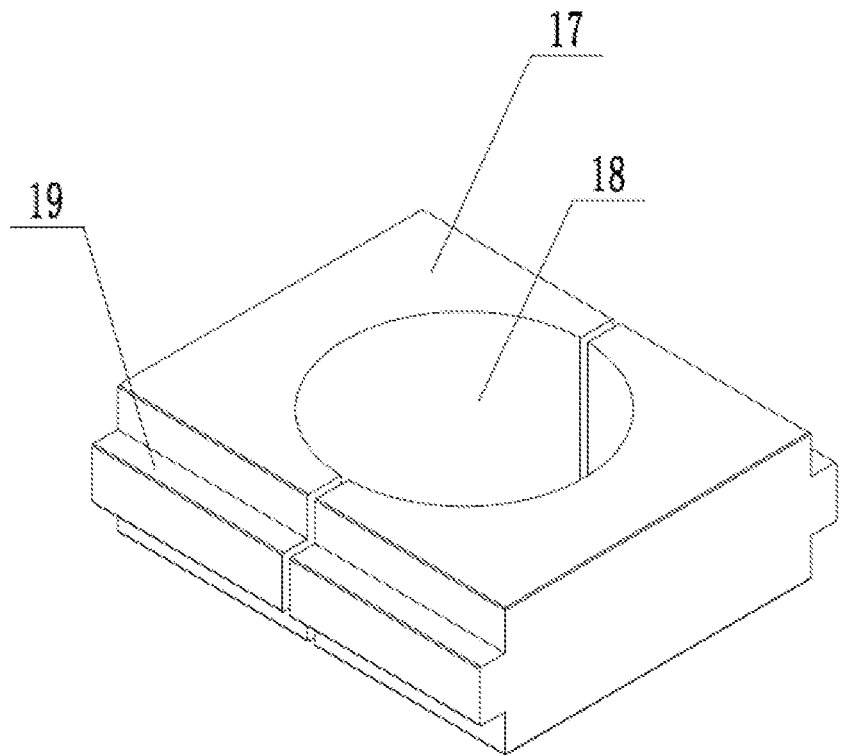
FIG. 12 is a second schematic diagram of a fixed block in the present disclosure.

As shown in FIG. 1 to FIG. 12, the embodiment provides a clamp 100. The clamp 100 comprises a box body 1, an opening 2 is formed in one side of the box body 1, two oppositely arranged clamping structures 3 are arranged in the box body 1, a sample 4 is arranged between the two clamping structures 3, each clamping structure 3 comprises an adjusting mechanism 5, and the distance between the two clamping structures 3 can be adjusted through the adjusting mechanism 5.

In the embodiment, each clamping structure 3 comprises a first clamping block 6, a second clamping block 7, a third clamping block 8 and a fourth clamping block 9, the first clamping block 6 and the second clamping block 7 are oppositely arranged, the third clamping block 8 and the fourth clamping block 9 are oppositely arranged, the first clamping block 6 is in contact with the third clamping block 8 and the fourth clamping block 9 respectively, the second clamping block 7 is in contact with the third clamping block 8 and the fourth clamping block 9 respectively, the third clamping block 8 and the fourth clamping block 9 are located between the first clamping block 6 and the second clamping block 7, the sample 4 is located between the first clamping blocks 6 of the two clamping structures 3, the second clamping blocks 7 of the two clamping structures 3 are connected with the box body 1, and the adjusting mechanism 5 is used for adjusting the distance between the third clamping block 8 and the fourth clamping block 9 so as to adjust the distance between the first clamping block 6 and the second clamping block 7.

In the embodiment, at least one elastic component 10 and at least one guide shaft 11 are arranged between the first clamping block 6 and the second clamping block 7, the elastic component 10 is a spring with high elastic modulus, the guide shaft 11 is a steel shaft. One end of the elastic component 10 is connected with the first clamping block 6, the other end of the elastic component 10 is connected with the second clamping block 7, and the guide shaft 11 is in sliding connection with the first clamping block 6 and the second clamping block 7. In the embodiment, the number of the elastic components 10 and the number of the guide shafts 11 are two, the guide shafts 11 are arranged inside the elastic components 10, the elastic components 10 are parallel to the guide shafts 11, the center lines of the elastic components 10 and the center lines of the guide shafts 11 are located on the same plane, and the center lines of the elastic components 10 and the center lines of the guide shafts 11 are parallel to the center line in the length direction of the box body 1. The length of the guide shaft 11 is not larger than the sum of the height of the first clamping block 6, the height of the second clamping block 7 and the length of the end face of the larger side of the third clamping block 8 or the fourth clamping block 9, namely, the length of the guide shaft 11 is not larger than the size H in FIG. 7.

In the embodiment, the adjusting mechanism 5 is a two-way screw rod, the adjusting mechanism 5 is located between the two guide shafts 11, the center line of the adjusting mechanism 5 is vertical to the center lines of the elastic components 10, the two-way screw rod passes through the third clamping block 8 and the fourth clamping block 9, a first threaded section of the two-way screw rod is in threaded connection with the third clamping block 8, a second threaded section of the two-way screw rod is in threaded connection with the fourth clamping block 9, the first threaded section and the second threaded section are opposite in screw directions, the two ends of the two-way screw rod extend into through holes 12 in the side walls of the box body 1, and at least one end of the adjusting mechanism 5 is provided with a bolt structure 21. In the embodiment, the bolt structures 21 are arranged at the two ends of the adjusting mechanism 5, the bolt structures 21 are hexagon socket screws, the bolt structures 21 are driven by bolt devices matched with the bolt structures 21 to rotate to adjust the distance between the third clamping block 8 and the fourth clamping block 9, and the bolt devices in the embodiment are Allen wrenches. The bolt structures 21 are arranged on the outer side, so that real-time dynamic adjustment in the test process can be conveniently realized at the exterior of the box body 1 through the Allen wrenches.

Specifically, due to the fact that the threads in the third clamping block 8 and the threads in the fourth clamping block 9 are opposite in direction, when the two-way screw rod is screwed through the Allen wrenches at the exterior, the third clamping block 8 and the fourth clamping block 9 move toward or away from each other. When the third clamping block 8 and the fourth clamping block 9 move toward each other, the distance between the third clamping block 8 and the fourth clamping block 9 is decreased, under the action of the force from the third clamping block 8 and the fourth clamping block 9, the first clamping block 6 and the second clamping block 7 move away from each other, namely, the distance between the first clamping block 6 and the second clamping block 7 is increased, and the two fixed blocks 17 move toward each other until gaps between the to-be-clamped sample 4 and the two fixed blocks 17 disappear, so that the purpose of clamping the sample 4 is achieved.

In the embodiment, the first clamping block 6 and the second clamping block 7 are the same in structures, each of the first clamping block 6 and the second clamping block 7 comprises a first inclined plane 13 and a second inclined plane 14, the third clamping block 8 and the fourth clamping block 9 are the same in structures, each of the third clamping block 8 and the fourth clamping block 9 comprises a third inclined plane 15 and a fourth inclined plane 16, the first inclined plane 13 of the first clamping block 6 is in contact with the third inclined plane 15 of the third clamping block 8, the second inclined plane 14 of the first clamping block 6 is in contact with the third inclined plane 15 of the fourth clamping block 9, the first inclined plane 13 of the second clamping block 7 is in contact with the fourth inclined plane 16 of the third clamping block 8, and the second inclined plane 14 of the second clamping block 7 is in contact with the fourth inclined plane 16 of the fourth clamping block 9.

In the embodiment, the guide shafts 11 guides the first clamping block 6 and the second clamping block 7 to move along the length direction of the box body 1. The free length of the elastic component 10 is less than the length of the guide shaft 11; when the length of the elastic component 10 is greater than the free length of the elastic component 10, the elastic component 10 is in a stretching state; when the elastic component 10 is in a stretching state, the elastic component 10 has a motion tendency to recover the free length, that is, the two elastic components 10 can play a role in ensuring that the first inclined surface 13 of the first clamping block 6 is always in contact with the third inclined surface 15 of the third clamping block 8, the second inclined surface 14 of the first clamping block 6 is always in contact with the third inclined surface 15 of the fourth clamping block 9, the first inclined surface 13 of the second clamping block 7 is always in contact with the fourth inclined surface 16 of the third clamping block 8, and the second inclined surface 14 of the second clamping block 7 is always in contact with the fourth inclined surface 16 of the fourth clamping block 9.

In the embodiment, the first inclined plane 13 and the second inclined plane 14 are symmetrical along the center line of the first clamping block 6 or the second clamping block 7, and the third inclined plane 15 and the fourth inclined plane 16 are symmetrical along the center line of the third clamping block 8 or the fourth clamping block 9.

In the embodiment, the cross section of the first clamping block 6 and the cross section of the second clamping block 7 are a trapezoid plus a rectangle respectively. The cross sections of the third clamping block 8 and the fourth clamping block 9 are trapezoidal, the length of the first clamping block 6 and the length of the second clamping block 7 are the same as the width of the interior of the box body 1, and the height of the first clamping block 6 and the height of the second clamping block 7 are the same as the height of the interior of the box body 1.

In the embodiment, two oppositely arranged fixed blocks 17 are arranged between the two clamping structures 3, the height of the fixed block 17 is the same as the height of the interior of the box body 1, the fixed block 17 is of a single structure, the structure is unchanged, the two fixed blocks 17 are both in sliding connection with the box body 1, the sample 4 is arranged between the two fixed blocks 17, and a cavity 18 formed by the two fixed blocks 17 is matched with the shape of the sample 4. In the embodiment, the sample 4 is of a cylindrical structure, and the shape of the opposite surfaces of the two fixed blocks 17 are semicircular arcs.

In the embodiment, protrusions 19 are arranged on the two sides of each fixed block 17, and the contact surface of each fixed block 17 and the first clamping block 6 is a plane. The distance between the ends of the two protrusions 19 of the same fixed block 17 are smaller than the outer width of the box body 1, and the distance between the shoulders of the two protrusions 19 of the same fixed block 17 are the same as the inner width of the box body 1. The protrusions 19 are located in sliding grooves 20 in the side walls of the box body 1, the length of each sliding groove 20 is more than twice of that of the protrusion 19, the width of the sliding groove 20 is greater than that of the protrusion 19, and the height of the sliding groove 20 is the same as that of the protrusion 19.

According to the embodiment, the clamp 100 can be dynamically adjusted in real time in the whole process of the rock mass discontinuity shear test of sedimentary rocks or parametamorphic rocks through the adjusting mechanism 5, the purpose of real-time tight seamless contact between the sample 4 and the fixed block 17 can be achieved, and therefore the requirement that shear loads can be truly and effectively transmitted to the sample 4 through the box body 1 is met.

Embodiment II

Figure 13:
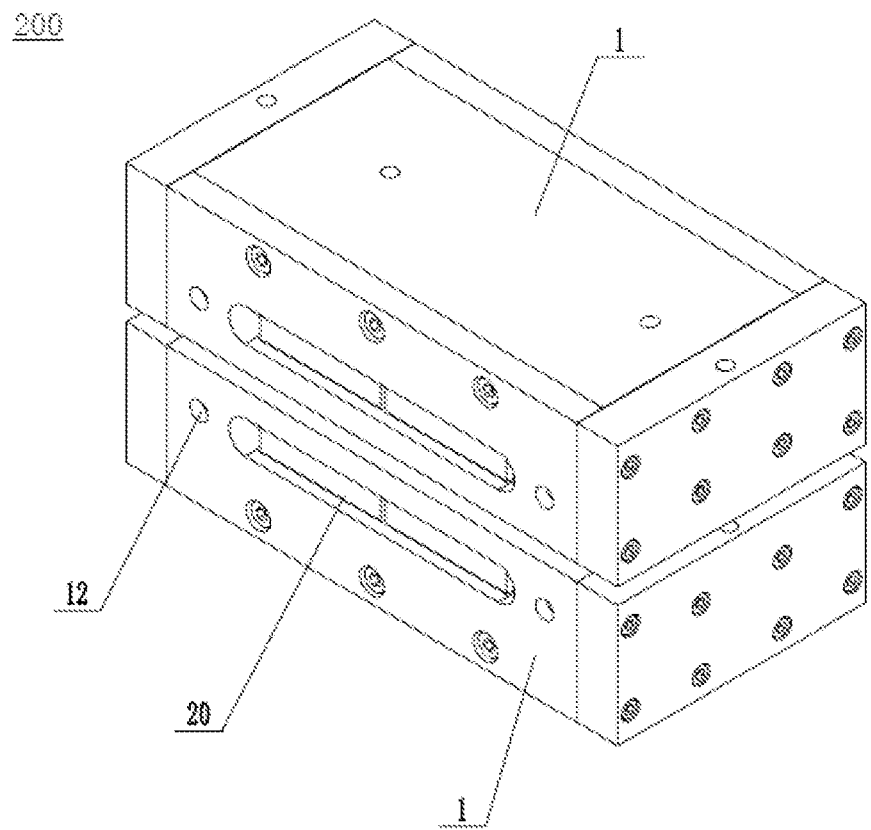
FIG. 13 is a schematic diagram of a shear test device in the present disclosure.
Figure 14:
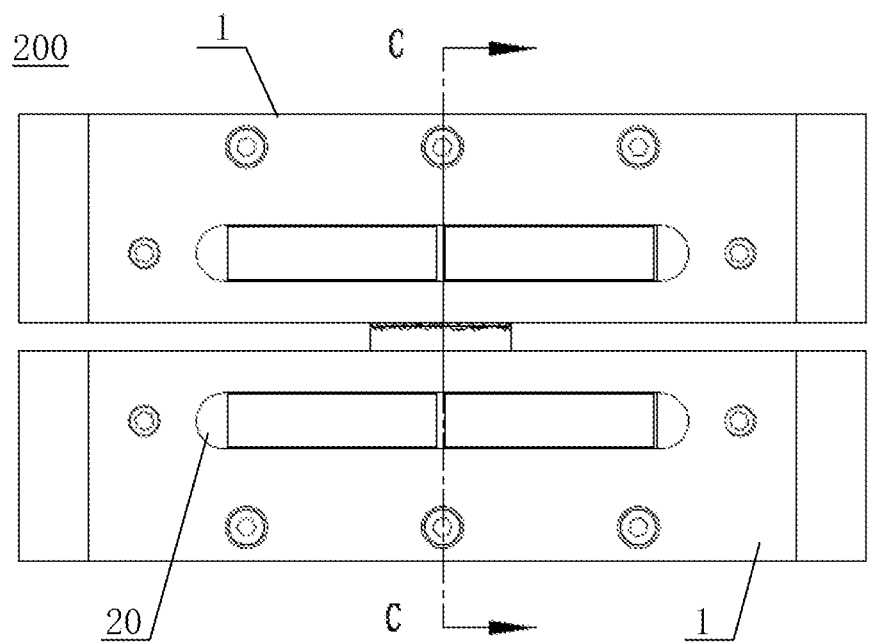
FIG. 14 is a front view of a shear test device in the present disclosure.
Figure 15:
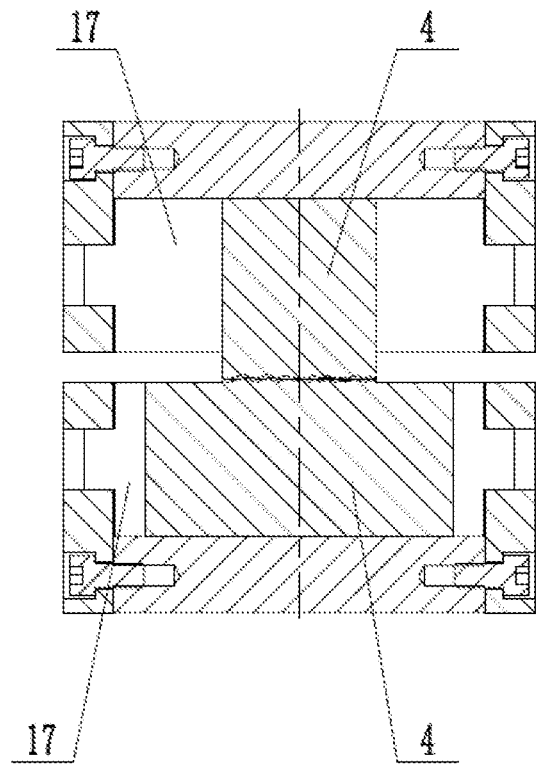
FIG. 15 is a cross-sectional view along the line C-C of FIG. 14.
Figure 16:
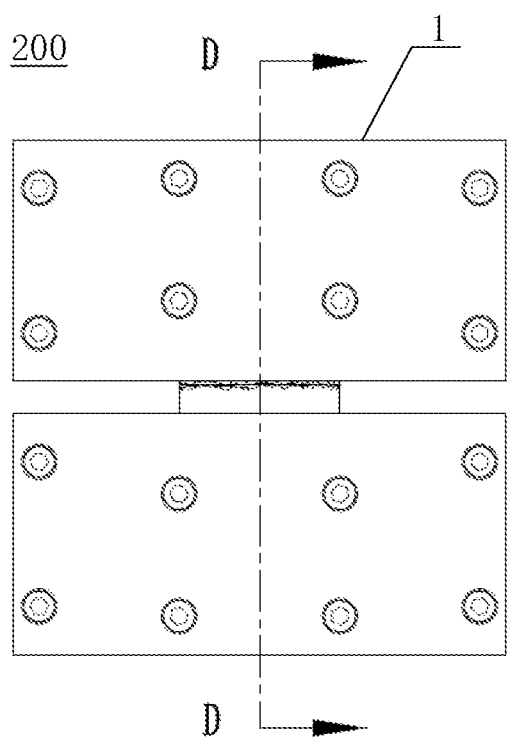
FIG. 16 is a side view of a shear test device in the present disclosure.
Figure 17:
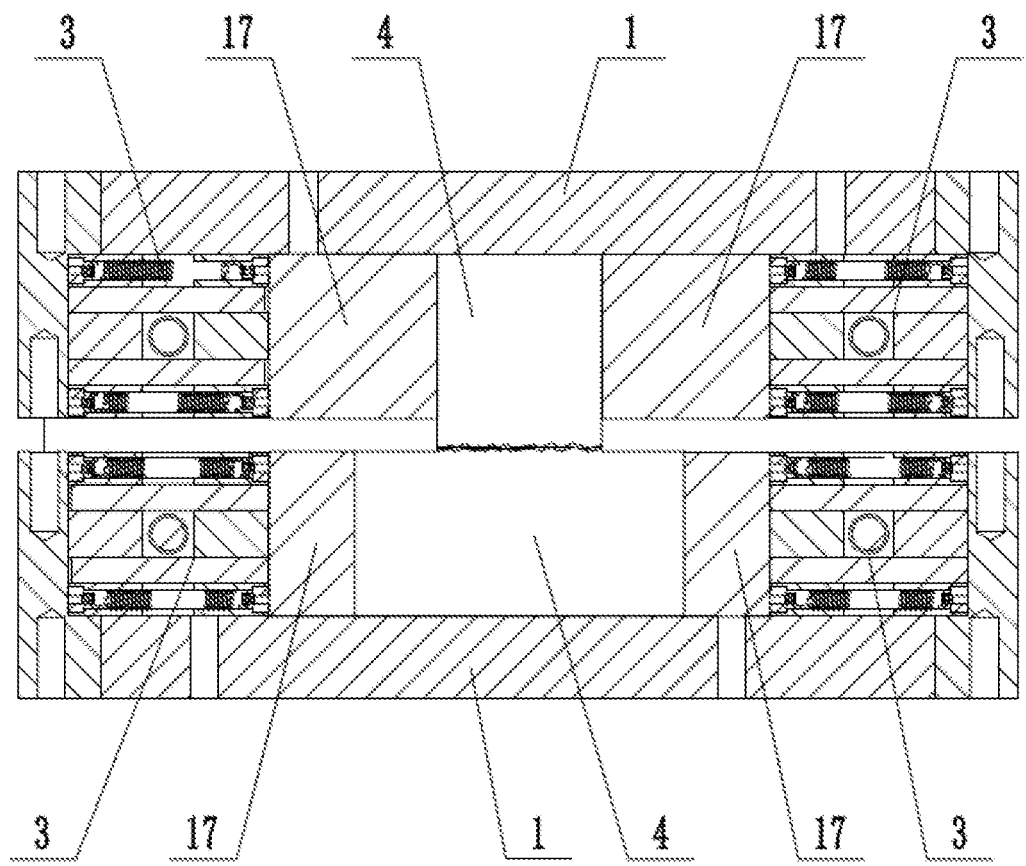
FIG. 17 is a cross-sectional view along the line D-D of FIG. 16.

As shown in FIG. 13 to FIG. 17, the embodiment provides a shear test device 200. The shear test device 200 comprises two clamps 100 in the first embodiment, the openings 2 of the two clamps 100 are arranged oppositely, and a gap is formed between the two clamps 100. The center lines of the two clamps 100 coincide, the clamping structures 3 on the left sides of the two clamps 100 are arranged oppositely, and the clamping structures 3 on the right sides of the two clamps 100 are arranged oppositely.

The shear test device 200 of the embodiment is used for performing a shear test on cylindrical samples 4 of sedimentary rocks or parametamorphic rocks. The upper cylindrical sample 4 is placed between the two upper fixed blocks 17, the lower cylindrical sample 4 is placed between the two lower fixed blocks 17. The diameter of the upper cylindrical sample 4 is smaller than that of the lower cylindrical sample 4, the height of the upper cylindrical sample 4 and the height of the lower cylindrical sample 4 are both greater than that of the clamp 100. The top surface of the upper cylindrical sample 4 is flat and straight, the bottom surface of the lower cylindrical sample 4 is flat and straight, the bottom surface of the upper cylindrical sample 4 is in the undulating rough form of the natural rock mass, the top surface of the lower cylindrical sample 4 is in the undulating rough form of the natural rock mass, the bottom surface of the upper cylindrical sample 4 is in contact with the top surface of the lower cylindrical sample 4, and the contact surface between the upper cylindrical sample 4 and the lower cylindrical sample 4 is the discontinuity of the sedimentary rocks or the parametamorphic rocks on which the rock mass shear test is to be performed.

Lubricating agents are evenly smeared between the upper clamping structure 3 and the top of the box body 1 and between the lower clamping structure 3 and the bottom of the box body 1 so as to reduce friction generated between the clamping structures 3 and the interior of the box body 1 during the adjustment process of the positions of the clamping structures 3.

In the mounting process of the sample, before testing, the upper cylindrical sample 4 is placed in the upper clamp 100, and the lower cylindrical sample 4 in the lower clamp 100; and through the adjusting mechanisms 5 for respectively adjusting the upper clamp 100 and the lower clamp 100, the upper cylindrical sample 4 and the lower cylindrical sample 4 are clamped.

In the test process, especially during the dynamic cyclic shear test process, when the two-way screw rod of the third clamping block 8 and the fourth clamping block 9 of the clamping structure 3 is loosened due to shear vibration and other factors, the distance between the third clamping block 8 and the fourth clamping block 9 is increased, the first clamping block 6 and the second clamping block 7 are prone to be separated from the third clamping block 8 and the fourth clamping block 9. At the moment, under the stretching action of the elastic component 10, the distance between the first clamping block 6 and the second clamping block 7 is reduced, so that a gap is generated between the clamping structure 3 and the fixed block 17, and then a gap is generated between the fixed block 17 and the sample 4. At the moment, the two-way screw rod on the side where the gap is generated is screwed through the Allen wrench at the exterior; and therefore, the requirement for eliminating the gap between the clamp 100 and the sample 4 in real time in the dynamic cyclic shear test process is met.

In the dismounting process of the sample 4, after the test, the two-way screw rod is adjusted through the Allen wrench at the exterior; due to the fact that the threads in the third clamping block 8 and the fourth clamping block 9 are opposite in directions, when the two-way screw rod is unscrewed through the Allen wrench, the third clamping block 8 and the fourth clamping block 9 move away from each other, namely, the distance between the third clamping block 8 and the fourth clamping block 9 is increased; the first clamping block 6 and the second clamping block 7 are prone to be separated from the third clamping block 8 and the fourth clamping block 9. At the moment, under the stretching action of the elastic component 10, the distance between the third clamping block 8 and the fourth clamping block 9 is reduced, so that a gap is generated between the clamping structure 3 and the fixed block 17, namely, the fixed block 17 is not restrained due to the action of the force from the clamping structure 3, and the sample 4 can be smoothly taken out from the clamp 100.

When the sample 4 is mounted or dismounted, no matter for the upper cylindrical sample 4 or the lower cylindrical sample 4, the bolt structures 21 on the outer sides of the front wall and the rear wall of the upper box body 1 or the lower box body 1 can be synchronously adjusted at the same time, so as to quickly screw or unscrew the two-way screw rod, and quickly mount or dismount the sample 4.

Specific examples are used for illustration of the principles and implementation methods of the present disclosure. The description of the above-mentioned embodiments is used to help illustrate the method and the core principles of the present disclosure; and, those skilled in the art can make various modifications in terms of specific embodiments and scope of application in accordance with the teachings of the present disclosure. In conclusion, the content of this specification shall not be construed as a limitation to the present disclosure.

What is claimed is:

1. A clamp, comprising:
   a box body,
   wherein an opening is formed in one side of the box body, two clamping structures are oppositely arranged in the box body, a sample is arranged between the two clamping structures, each clamping structure comprises an adjusting mechanism, and a distance between the two clamping structures is adjusted through adjusting mechanisms of the two clamping structures;

wherein each clamping structure comprises a first clamping block, a second clamping block, a third clamping block and a fourth clamping block, the first clamping block and the second clamping block are oppositely arranged, the third clamping block and the fourth clamping block are oppositely arranged, the first clamping block is in contact with the third clamping block and the fourth clamping block, the second clamping block is in contact with the third clamping block and the fourth clamping block, the third clamping block and the fourth clamping block are located between the first clamping block and the second clamping block, the sample is located between the first clamping blocks of the two clamping structures, the second clamping blocks of the two clamping structures are both connected with the box body, and the adjusting mechanism is used for adjusting a distance between the third clamping block and the fourth clamping block so as to adjust a distance between the first clamping block and the second clamping block;

wherein at least one elastic component and at least one guide shaft are arranged between the first clamping block and the second clamping block, one end of the elastic component is connected with the first clamping block, other end of the elastic component is connected with the second clamping block, and the guide shaft is in sliding connection with the first clamping block and the second clamping block; and wherein the adjusting mechanism is a two-way screw rod, the two-way screw rod is passed through and arranged in the third clamping block and the fourth clamping block, a first threaded section of the two-way screw rod is in threaded connection with the third clamping block, a second threaded section of the two-way screw rod is in threaded connection with the fourth clamping block, the first threaded section and the second threaded section are opposite in screw directions, two ends of the two-way screw rod extend into through holes in side walls of the box body, at least one end of the adjusting mechanism is provided with a bolt structure, and a bolt device drives the bolt structures to rotate to adjust the distance between the third clamping block and the fourth clamping block.

2. The clamp according to claim 1, wherein the first clamping block and the second clamping block are same in structures, each of the first clamping block and the second clamping block comprises a first inclined plane and a second inclined plane, the third clamping block and the fourth clamping block are same in structures, each of the third clamping block and the fourth clamping block comprises a third inclined plane and a fourth inclined plane, the first inclined plane of the first clamping block is in contact with the third inclined plane of the third clamping block, the second inclined plane of the first clamping block is in contact with the third inclined plane of the fourth clamping block, the first inclined plane of the second clamping block is in contact with the fourth inclined plane of the third clamping block, and the second inclined plane of the second clamping block is in contact with the fourth inclined plane of the fourth clamping block.

3. The clamp according to claim 2, wherein the first inclined plane and the second inclined plane are symmetrical along a center line of the first clamping block or the second clamping block, and the third inclined plane and the fourth inclined plane are symmetrical along a center line of the third clamping block or the fourth clamping block.

4. The clamp according to claim 3, wherein cross sections of the third clamping block and the fourth clamping block are trapezoidal.

5. The clamp according to claim 1, wherein two fixed blocks are oppositely arranged between the two clamping structures, the two fixed blocks are both in sliding connection with the box body, the sample is arranged between the two fixed blocks and a cavity formed by the two fixed blocks is matched with a shape of the sample.

6. The clamp according to claim 5, wherein protrusions are arranged on two sides of each fixed block and located in sliding grooves in side walls of the box body.

7. A shear test device, comprising two clamps according to claim 1, wherein openings of two clamps are oppositely arranged, and a gap is formed between the two clamps.

8. The shear test device according to claim 7, wherein the first clamping block and the second clamping block are same in structures, each of the first clamping block and the second clamping block comprises a first inclined plane and a second inclined plane, the third clamping block and the fourth clamping block are same in structures, each of the third clamping block and the fourth clamping block comprises a third inclined plane and a fourth inclined plane, the first inclined plane of the first clamping block is in contact with the third inclined plane of the third clamping block, the second inclined plane of the first clamping block is in contact with the third inclined plane of the fourth clamping block, the first inclined plane of the second clamping block is in contact with the fourth inclined plane of the third clamping block, and the second inclined plane of the second clamping block is in contact with the fourth inclined plane of the fourth clamping block.

9. The shear test device according to claim 8, wherein the first inclined plane and the second inclined plane are symmetrical along a center line of the first clamping block or the second clamping block, and the third inclined plane and the fourth inclined plane are symmetrical along a center line of the third clamping block or the fourth clamping block.

10. The shear test device according to claim 9, wherein cross sections of the third clamping block and the fourth clamping block are trapezoidal.

11. The shear test device according to claim 7, wherein two fixed blocks are oppositely arranged between the two clamping structures, the two fixed blocks are both in sliding connection with the box body, the sample is arranged between the two fixed blocks, and a cavity formed by the two fixed blocks is matched with a shape of the sample.

12. The shear test device according to claim 11, wherein protrusions are arranged on two sides of each fixed block and located in sliding grooves in side walls of the box body.

* * * * *